United States Patent [19]
Shibatani et al.

[11] Patent Number: 5,487,996
[45] Date of Patent: Jan. 30, 1996

[54] GENE CODING FOR ESTERASE AND NOVEL MICROORGANISM CONTAINING SAID GENE

[75] Inventors: Takeji Shibatani, Kobe; Saburo Komatsubara, Kawaguchi; Kenji Omori, Takatsuki; Hiroyuki Akatsuka, Moriguchi, all of Japan

[73] Assignee: Tanabe Seiyaku Co., Ltd., Osaka, Japan

[21] Appl. No.: 272,875

[22] Filed: Jul. 11, 1994

Related U.S. Application Data

[63] Continuation of Ser. No. 980,516, Nov. 25, 1992, abandoned.

[30] Foreign Application Priority Data

Nov. 25, 1991 [JP] Japan .................................. 3-355440
Apr. 13, 1992 [JP] Japan .................................. 4-137502

[51] Int. Cl.⁶ .............................. C12N 1/20; C12N 1/21
[52] U.S. Cl. .................... 435/252.1; 435/252.3; 435/252.33; 435/196; 435/197
[58] Field of Search .................... 435/196, 197, 435/320.1, 252.3, 252.33, 252.1; 530/23.2

[56] References Cited

U.S. PATENT DOCUMENTS 5,208,156  5/1993  Shibatani et al. ..................... 423/196

FOREIGN PATENT DOCUMENTS 446771  9/1991  European Pat. Off. .
382125  7/1991  Japan .
606743  11/1986  WIPO .

OTHER PUBLICATIONS

Okabayashi, T., et al, (1970) Biochem. Biophys. Acta. 220, 116–123.
Goullet, P. (1981) J. Gen. Microbiol. 127, 161–167.
Goullet, P., et al (1990) J. Gen. Microbiol. 136, 431–440.
Monget, D. (1981) Chem. Abst. 95:147054r.
Reddy, P. G., et. al. (1989) Gene 26, 145–152.
Choi, K. D., et. al. (1990) Agric. Biol. Chem. 54(8), 2039–2045.
Hong, K. H. et. al. (1991) Agric. Biol. Chem. 55(11), 2839–2845.
Chihara– Siomi, M,. et. al. (1992) Arc. Biochem. Biophys, 296(2), 505–513.
Bohne et al., Arch. Microbiol., 121, pp. 181–186 (1979).
Biochem. Biophys. Res. Commun., vol. 141, pp. 185–190 (1986).

Primary Examiner—Charles L. Patterson, Jr.
Attorney, Agent, or Firm—Birch, Stewart, Kolasch & Birch

[57] ABSTRACT

A gene encoding an esterase originated from a microorganism of the genus Serratia, a mutant strain having high esterase productivity containing said gene, a recombinant plasmid comprising said gene inserted into a vector plasmid, a novel microorganism transformed with said recombinant plasmid, and a method for the production of an esterase which comprises cultivating the mutant strain or the novel microorganism as set forth above in a medium and collecting the produced esterase outside and inside the cells. Said mutant strain having high esterase productivity and new transformed microorganism have excellent esterase productivity and can produce the desired esterase in high purity on a large scale.

3 Claims, 2 Drawing Sheets

Fig. 1

Fig. 2 pLIPE111 pLIPE121 pLIPE131 pLIPE141 pLIPE151

GENE CODING FOR ESTERASE AND NOVEL MICROORGANISM CONTAINING SAID GENE

This application is a continuation of application Ser. No. 07/980,516 filed on Nov. 25, 1992, now abandoned.

This invention relates to a gene coding for an esterase, a recombinant plasmid containing said gene, a novel microorganism transformed with the recombinant plasmid, and a process for producing an esterase by cultivating the microorganism.

Prior Art

Recently, it has frequently been tried to utilize enzymes such as esterase in hydrolysis reaction. For such a purpose, there are known various esterases, for example, esterases originated from animals (e.g. pig liver, pig pancreas, etc.), and esterases originated from microorganisms, such as *Arthrobacter globiformis, Geotrichum candidum, Candida cylindracea, Pseudomonas fluorescens*, etc.

Further, it is known that an esterase is obtained by utilizing a recombinant DNA technology in microorganism, such as *Rhizopus delemar* (cf. Japanese Patent First Publication (Kokai) No. 87175/1991), *Pseudomonas fragi* (cf. Biochemical and Biophysical Research Communications, Vol. 141, 185–190 (1986)).

However, the known esterases or known methods for producing esterase have various problems. For instance, animal-origin esterases are very expensive. Besides, above-mentioned microorganisms-origin esterases of the genus Arthrobacter, Geotrichum, Candida, Pseudomonas, or Rhizopus had problems such that they were disadvantageous in activity, stability, or specificity, or that the esterase-producing microorganism had no high productivity.

As a result of various investigations, the present inventors found that the desired esterase can be produced favorably by utilizing recombinant DNA technology in a microorganism of the genus Serratia. That is, the present inventors have succeeded to obtain a gene coding for an esterase from a microorganism of the genus Serratia, and have found that a transformed microorganism having a significantly increased esterase productivity can be obtained by introducing the recombinant plasmid containing the said gene into a host microorganism, and further have found that the desired esterase can be produced by using said transformed microorganism on an industrial scale.

SUMMARY DESCRIPTION OF THE INVENTION

An object of the invention is to provide a gene coding for an esterase originated from a microorganism of the genus Serratia. Another object of the invention is to provide a mutant strain which has a high productivity of esterase. Another object of the invention is to provide a recombinant plasmid produced by inserting said gene into a vector plasmid. A further object of the invention is to provide a transformed microorganism containing said recombinant plasmid. A still further object of the invention is to provide a method for the production of an esterase by cultivating said transformed microorganism and collecting the produced esterase outside and inside the cells of the microorganism.

DETAILED DESCRIPTION OF THE INVENTION

The gene encoding an esterase originated from a microorganism of the genus Serratia of this invention and is a double stranded DNA of 1839 base pairs having an open reading frame, specifically DNAs having the nucleotide sequences shown in SEQ ID NO: 1 and SEQ ID NO: 2 hereinafter.

The donor microorganisms for such a gene encoding an esterase include any microorganisms belonging to the genus Serratia which has an esterase productivity, for example, *Serratia marcescens* Sr41 (FERN BP-487), *Serratia liquefaciens* ATCC 27592, *Serratia marcescens* ATCC 13880, *Serratia marcescens* ATCC 14764, *Serratia marcescens* ATCC 19180, *Serratia marcescens* ATCC 21074, *Serratia marcescens* ATCC 27117, *Serratia marcescens* ATCC 21212, etc.

The donor microorganism includes also mutant strains derived from wild strains, such as various amino acid-requiring strains, various nucleic acid-requiring strains, various vitamin-requiring strains, and the like, for example, *Serratia marcescens* M-1 (FERM BP-4068). Said *Serratia marcescens* M-1 has more than two fold higher esterase productivity than the parent strain *Serratia marcescens* Sr41 and contains an esterase gene coded by the DNA sequence of SEQ ID NO:2. The mutant strain M-i can be obtained by treating the parent *Serratia marcescens* Sr41 (FERM BP-487) with N-methyl-N'-nitro-N-nitrosoguanidine (NTG) according to a method of Aderburg et al. [Biochemical and Biophysical Research Communications, Vol. 18, 788 (1965)], cultivating the thus treated microorganism on an agar medium containing emulsified triglyceride, and collecting the colony around which the largest clear zone is formed. In the same manner, another mutant strain *Serratia marcescens* G205 having 1.5 fold or higher esterase-productivity can be obtained from the parent strain *Serratia marcescens* Sr41.

The vector plasmid to be inserted with the gene encoding an esterase includes any plasmids which are replicable in transformed cells, but is preferably plasmids which have a copy number of 1 to several thousands and contain a resistant marker against antibiotics such as ampicillin, kanamycin, chloramphenicol, and further contain an appropriate promoter such as lac, tac, or trp. Moreover, the vector plasmids may further contain a plasmid stabilizing gene such as par and parB.

These vector plasmids include, for example, pLG339 [Gene, Vol. 18,332 (1982)], pBR322 [Gene, Vol. 2, 95 (1977)], pUC18 [Gene, Vol. 33, 103 (1985)], pUC19 [Gene, Vol. 33, 103 (1985], pHSG298 [Gene, Vol. 61, 63 (1987)], pHSG299 [Gene, Vol. 61, 63 (1987)], and the like.

The above vector plasmids are commercially available or can be obtained from microbial cells containing these plasmids by a conventional method, for example, by "cleared lysate method" (cf. Yasuyuki Takagi, "Procedure for Experiment in Genetic Engineering", page 125, published by Kodansha, 1980), or by "alkaline lysis method" [cf. Maniatis et al., "Molecular Cloning", page 368, Cold Spring Harbor Laboratory, U.S.A. (1982)].

The host microorganisms (both for the recombination of plasmids and for the expression of the desired esterase), include any microorganisms which can be transformed with the recombinant plasmid and can replicate the plasmid therein, and can express the gene on the plasmid and can produce a functional protein. These host microorganisms are, for example, microorganisms belonging to the genus Serratia or the genus Escherichia, specifically *Serratia marcescens* Sr41 and various mutant strains derived therefrom, for example, *Serratia marcescens* M-1, *Serratia marcescens* TT392 [ cf. Journal of Bacteriology, Vol. 161, 1 ( 1985)], or *Escherichia coli* K12 DH5 [cf. Maniatis et al., "Molecular Cloning", 2nd volume, A10, Cold Spring Harbor Laboratory, U.S.A. (1989)].

The chromosomal DNA containing the gene encoding an esterase can easily be obtained from microorganisms containing said gene by a conventional method, for example, by treating the microbial cells with a lysozyme and further with a surfactant (e.g. sodium lauryl sulfate, sodium N-lauroyl sarcosinate, etc.), extracting the cells thus treated with an organic solvent (e.g. phenol, chloroform, diethyl ether, etc.) to remove proteins, and then precipitating the DNA with ethanol [cf. Journal of Molecular Biology, Vol. 3, 208 (1961), and Biochimica et Biophysica Acta, Vol. 72, 619 (1963)].

The recombinant plasmid comprising the chromosomal DNA containing a gene encoding esterase and the vector plasmid can easily be prepared by a conventional method, for example, by cleaving the chromosomal DNA and the plasmid DNA with an appropriate restriction endonuclease (e.g. EcoRI, BamHI, HindIII, SalI, etc.) and then treating the resultant with DNA ligase (e.g. T4 DNA ligase, *E. coli* DNA ligase, etc.), if required, after treating the resultant with a terminal transferase or DNA polymerase [cf. Methods in Enzymology, Vol. 68, 41 (1979), and Yasuyuki Takagi, "Procedure for Experiment in Genetic Engineering", page 135, published by Kodansha, 1980].

Selection of the desired recombinant plasmid containing the esterase gene from a mixture of recombinant plasmids obtained by the above procedure can be done as follows.

Microbial cells being restriction endonuclease deficient and having no esterase activity (e.g. *Escherichia coli* K12 DH5) are transformed with the above mixture of recombinant plasmids, and the thus-transformed cells are spread onto an agar medium containing an emulsified triglyceride, for example, a nutrient agar medium containing tributyrin emulsified with polyoxyethylene cetyl alcohol ether (Brij 58) and also containing a prescribed concentration of an antibiotic. After incubation at 30° to 37° C. for 1 to 2 days, the colony of a transformant around which a large clear zone is formed is isolated.

The above introduction of the recombinant plasmid into the host microorganism is carried out by a conventional method, for example, by treating the host cells with an aqueous calcium chloride solution at a low temperature to increase the membrane permeability of the cells and then introducing the recombinant plasmid into the host cells [cf. Journal of Molecular Biology, Vol. 53, 159 (1970)], or by an electroporation method.

Then, the plasmid DNA is extracted from the transformant by "alkaline lysis method" to give a recombinant plasmid containing the gene encoding an esterase.

In order to make the transformation efficient, the recombinant plasmid thus obtained is modified in a microorganism which is restriction endonuclease deficient and is the same species of the host microorganism to be used for expressing the esterase. That is, when the host microorganism to be used is *Serratia marcescens* Sr41, the recombinant plasmid obtained above is introduced into *Serratia marcescens* TT392, which is restriction enzyme deficient strain. The recombinant plasmid thus modified is isolated from the microorganism.

The modified recombinant plasmid is then introduced into a host microorganism to obtain the desired transformant suitable for the production of the desired esterase.

The introduction of the recombinant plasmid into the host microorganism can easily be done by the method of Takagi & Kizumi [cf. Journal of Bacteriology, Vol. 161, 1 (1985)]. The host microorganisms to be used for said transformation include the above-mentioned microorganisms but are preferably strains having high esterase productivity. The desired transformant can be obtained by isolating the colony expressing antibitotics resistance.

The transformed microorganisms obtained by the above-mentioned method are, for example, *Serratia marcescens* TA5025 (FERM BP-4067) which is obtained by introducing a recombinant plasmid consisting of pUC19 and the 2.8 kb SalI-BamHI DNA fragment containing an esterase gene into *Serratia marcescens* Sr41; *Serratia marcescens* TBE101 which is obtained by introducing a recombinant plasmid consisting of pBR322 and the 4.0 kb SalI DNA fragment containing an esterase gene into *Serratia marcescens* Sr41. These transformed strains all have the same morphological characteristics as those of the host microorganism *Serratia marcescens* Sr41.

The production of esterase with the transformed microorganism obtained above is carried out by cultivating the microorganism in a medium and collecting the esterase outside and inside the cells of the microorganism.

The medium used for the production of esterase includes any conventional medium wherein the microorganism can grow. Suitable medium contains a carbon source such as saccharides (e.g. glucose, sucrose, molasses, etc.), organic acids (e.g. fumaric acid, citric acid, etc.), alcohols (e.g. glycerol, etc.), or amino acids (e.g. alanine, glutamine, asparagine, etc.) and a nitrogen source such as inorganic ammonium salts (e.g. ammonium sulfate, ammonium chloride, etc.), urea, peptone, corn steep liquor, yeast extract, casein hydrolysate, and the like. The carbon source is usually contained in an amount of 1 to 15% by weight based on the whole weight of the medium, and the nitrogen source is usually contained in an amount of 0.1 to 2.0% by weight based on the whole weight of the medium. The medium may optionally contain further an appropriate amount of an inorganic salt (e.g. phosphate, magnesium salt, potassium salt, calcium salt, etc.) and/or a metallic ion (e.g. iron, manganese, copper, zinc, etc.). In case of a synthetic medium, it may further contain vitamins or amino acids, and further, inducers for esterase production (e.g. vegetable oils, surfactants, etc.), defoaming agents, antibiotics which are suitable for stabilizing the recombinant plasmid in microorganisms. The medium is preferably adjusted to a pH 5 to 8.

The cultivation of the transformed microorganism is carried out by a conventional method. For example, the microorganism is inoculated into a medium and is cultivated by shaking culture, aeration culture, standing culture, and the like. The cultivation conditions may vary depending on the kinds of the medium and cultivation methods, but may be any conditions suitable for growth of the microorganism, usually at the initial pH 5–8, at 20° to 40° C. for 1 to 2 days.

The esterase produced outside and inside the cultivated cells is collected by a conventional method. For example, the esterase contained in the medium is collected by means of salting out with an inorganic salt, precipitation with an organic solvent, absorption or desorption with ion exchange resin and various column chromatography, gel filtration, use of protein-precipitating agent, or a combination of these methods. The esterase accumulated within the cells is obtained by firstly disrupting the cells by a physical method such as frictional disrupting device (Dyno Mill) or a chemical means such as treatment with lysozyme, and then collecting the esterase in the cell extract by the above-mentioned method.

The gene encoding the esterase of this invention is not limited to those of the DNA sequences disclosed specifically in the present specification but includes any gene having a DNA sequence obtained by modifications in the sequence such as insertion, deletion, substitution. That is, the esterase gene may artificially be modified directly in a test tube by using a synthetic mutated DNA primer designed on the basis of the DNA sequence of the esterase gene specifically disclosed herein, or by using a chemical mutating agent such as formic acid, hydrazine sulfite. Further, a mutant gene may be obtained by treating an esterase producing strain with NTG or UV.

EXAMPLES

The present invention is illustrated by the following Examples but should not be construed to be limited thereto.

In the Examples, the esterase activity was measured by a convenient method (using Lipase Kit S, manufactured by Dainippon Pharmaceutical Co., Ltd., Japan). It was also measured by another method comprising subjecting the product to enzymatic reaction in olive oil (as a substrate) at pH 8.0, 37° C. for 20 minutes, and then measuring the amount of formed fatty acid. The unit of esterase activity was expressed as μmols of fatty acid formed per minute. Besides, the medium used in Examples has the following formulation, wherein "%" is W/V % unless specified otherwise.

LB medium: 1.0% of Bactotryptone (manufactured by Difco), 0.5% of Bacto Yeast Extract (manufactured by Difco), and 0.5% of sodium chloride.

LBG plate medium: 1.0% of Bactotryptone (manufactured by Difco), 0.5% of Bacto Yeast Extract (manufactured by Difco), 0.5% sodium chloride, and 1.0% of Gellan Gum (manufactured by Wako Pure Chemical Industries, Ltd., Japan).

Tributyrin-containing LBG plate medium: LBG plate medium containing 0.5 v/v % of tributyrin, 0.5% of polyoxyethylene cetyl alcohol ether, and 0.005% of ampicillin.

Esterase producing medium: 1.0% of dextrin, 2.0% of Meast (a tradenamed yeast extract, manufactured by Asahi Breweries, Ltd.), 0.2% of ammonium sulfate, 0.1% of potassium dihydrogen phosphate, 0.05% of magnesium sulfate heptahydrate, 0.01% of calcium chloride dihydrate, 0.001% of ferrous sulfate hepta hydrate, 0.5% of Tween 80, and 0.1% of colorin.

Example 1

(1) Preparation of chromosomal DNA containing a gene encoding an esterase:

*Serratia marcescens* Sr41 (FERM BP-487) was subjected to aerobic shaking culture in LB medium (200 ml) at 30° C. overnight, and then the cells were collected by centrifugation. The cells were suspended in 0.9% aqueous sodium chloride solution (200 ml) once and then collected by centrifugation in order to wash them. The cells thus washed were suspended in an aqueous solution of 50 mM Tris-HCl-50 mM disodium ethylenediamine tetraacetate (pH 7.5, 200 ml) containing 200 mg of lysozyme, and the mixture was allowed to stand at room temperature for one hour.

To the mixture was added sodium lauryl sulfate in a concentration of 0.5%, and thereto was further added Protenase K, and the mixture was mildly shaken at 50° C. for 3 hours to lyse the cells. The mixture was extracted twice with an equal volume of phenol saturated with an aqueous solution of 10 mM Tris-HCl-1 mM disodiumethylenediamine tetraacetate (pH 8.0) (hereinafter, referred to as "TE"), and further extracted twice with a mixture of equal volume of TE-saturated phenol and chloroform, and then the resultant aqueous phase was subjected to precipitation with ethanol. The precipitate was dissolved in TE to prepare a TE solution containing 2.5 mg of the chromosomal DNA containing a gene encoding an esterase.

(2) Preparation of a recombinant plasmid DNA:

The chromosomal DNA prepared in the above (1) (20 μg) was completely digested with restriction endonuclease SalI, which was extracted twice with a mixture of equal volume of TE-saturated phenol and chloroform. To the mixture was added 0.5 volume of 7.5M ammonium acetate, and the DNA was recovered by centrifugation with two times volume of ethanol.

DNA (0.5 μg) of plasmid vector pUC19, which was completely digested with the same restriction enzyme as above, was dephosphated by treating with alkaline phosphatase (manufactured by Takara Shuzo Co., Ltd., Japan, 0.4 unit) at 56° C. for one hour, and the resultant was extracted twice with a mixture of equal volume of TE-saturated phenol and chloroform, and thereto was added 0.5 volume of 7.5M ammonium acetate, and then the vector plasmid DNA was recovered by precipitating with two volumes of ethanol. The dephosphated plasmid vector thus obtained was mixed with the chromosomal DNA obtained above (3 μg) and ligated with a DNA ligation kit (manufactured by Takara Shuzo Co., Ltd.) at 4° C. for 16 hours to give the recombinant plasmid DNA.

(3) Transformation with the recombinant plasmid and preparation of colony bank with *E. coli* host:

The cells of *E. coli* DH5 were treated by the method of Hanahan [cf. Journal of Molecular Biology, Vol. 166, 557 (1983)] and thereto was added the reaction mixture containing a plasmid DNA obtained in the above (2), by which the transformation was effected. The cells thus treated were spread onto LBG plate medium containing ampicillin (50 μg/ml), and they were incubated at 37° C. overnight to give the transformant (about 20,000 strains) containing recombinant plasmids inserted with fragments of the chromosomal DNA of *Serratia marcescens* Sr41.

(4) Isolation and identification of a transformant strain containing a gene encoding an esterase:

When an esterase producing strain is inoculated to a tributyrin-containing LBG plate medium, the esterase produced in the medium decomposes tributyrin to give fatty acids, by which the triglyceride emulsion around the colony is modified to form a circular clear zone around the colonies. By utilizing this phenomenon, the screening of transformants was effected.

The transformants (about 20,000 strains) obtained in the above (3) were inoculated to a tributyrin-containing LBG plate medium, which was incubated at 37° C. overnight, by which one strain forming a clear zone was isolated from the DNA bank of SalI.

The formation of this clear zone will be owing to the activity of esterase, because when *Serratia marcescens* Sr41 was inoculated to a tributyrin-containing LBG plate medium and incubated at 37° C. overnight, the formation of a clear zone was observed, but when the untransformed *E. coli* DH5 and the *E. Coli* DH5 carrying a plasmid vector pUC19 were inoculated to a tributyrin-containing LBG plate medium and incubated at 37° C. overnight, no formation of a clear zone was observed.

Besides, the transformant being capable of formation of a clear zone was cultivated in a LB medium (60 ml) containing ampicillin (200 μg/ml) by aerobic shaking culture at 37° C. overnight, and the cells were collected and suspended in a 200 mM Tris-HCl buffer solution (pH 8.0, 20 ml). After disruption of the cells by sonication, the esterase activity of the mixture was measured by the convenient method. As a result, there was observed $1.5 \times 10^3$ units of esterase activity.

Moreover, the mixture obtained above was subjected to an electrophoresis with SDS polyacrylamide gel. As a result, the product showed a new band, which was not shown in the product from *E. coli* DH5 containing only vector plasmid, at the same position as that in the partially purified standard esterase obtained from the supernatant of the culture of *Serratia marcescens* Sr41.

Example 2

Analysis of plasmid:

A plasmid DNA was prepared from the cells of the transformant obtained in Example 1-(4) by a conventional method [cf. Maniatis et al., "Molecular Cloning", page 368, Cold Spring Harbor Laboratory, U.S.A. (1982)], cleaved with various restriction endonucleases and then subjected to an agarose gel electrophoresis. As a result, it was confirmed that this plasmid (hereinafter, referred to as "pLIPE101") contained a SalI DNA fragment of about 4.0 kb.

Figure 1:
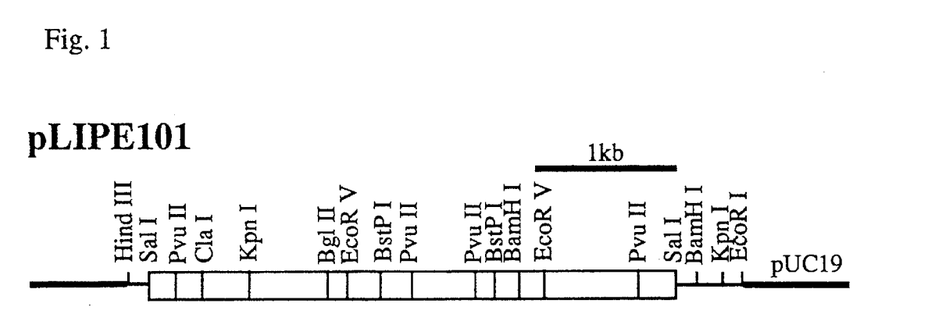
FIG. 1 shows a restriction endonuclease map of the plasmid DNA pLIPE101 isolated from the recombinant cells in Example 2.

The restriction endonuclease map of the recombinant DNA fragment of about 4.0 kb contained in pLIPE101 is shown in the accompanying FIG. 1.

The SalI DNA fragment of about 4.0 kb of the plasmid pLIPE101 was cleaved with various restriction endonucleases, and each DNA fragment was subcloned into plasmid vector pUC19, followed by transformation of *E. coli* DH5 therewith. The transformants were cultivated in a tributyrin-containing LBG plate medium in the same manner as described above, and it was determined whether a clear zone was formed or not.

Figure 2:
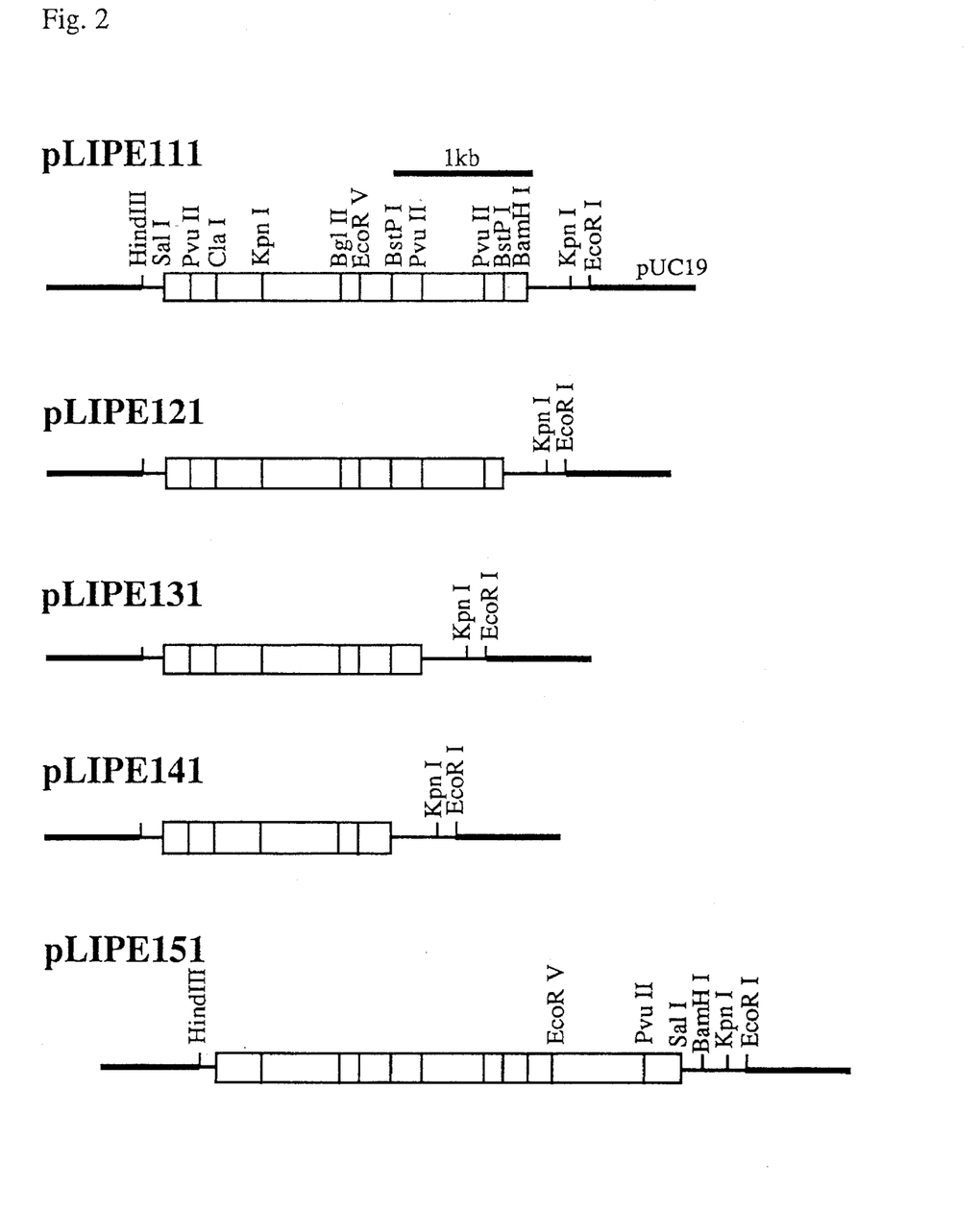
FIG. 2 shows restriction endonuclease maps of each of plasmid DNAs, pLIPE111, pLIPE121, pLIPE131, pLIPE141, and pLIPE151, which were produced by deleting the plasmid DNA pLIPE101 using a restriction endonuclease and DNA ligase.

The restriction endonuclease maps of each DNA fragment are shown in the accompanying FIG. 2. As to *E. coli* DH5 transformed with the plasmid containing SalI-BamHI DNA fragment of about 2.8 kb (pLIPE111) and the strain transformed with the plasmid containing SalI-BstPI DNA fragment of about 2.6 kb (pLIPE121), there were observed the formation of a clear zone and esterase activity (measured by the convenient method). However, as to *E. coli* DH5 transformed with the plasmid containing SalI-PvuII DNA fragment of about 1.9 kb (pLIPE131), the plasmid containing SalI-BstPI DNA fragment of about 1.7 kb (pLIPE141), and the plasmid containing ClaI-SalI DNA fragment of about 3.6 kb (pLIPE151), there was observed neither the formation of a clear zone nor esterase activity (measured by the convenient method).

It was found from the above results that the gene encoding an esterase originated from *Serratia marcescens* Sr41 was present in the SalI-BstPI DNA fragment of about 2.6 kb.

Example 3

Analysis of clone DNA:

[Determination of nucleotide sequence]

The recombinant plasmid pLIPE121 was treated with Kilobase Deletion Kit (manufactured by Takara Shuzo Co., Ltd.) to prepare various deletion plasmids. These plasmids thus obtained were subjected to annealing of a primer, synthesis of complementary chain with Klenow fragment of DNA polymerase [labelled with $(\alpha^{-32}P)$dCTP ($14.8 \times 10^6$ Bq/pmol, $74 \times 10^4$ Bq)] according to the dideoxy chain termination method of Sanger et al. [Proc. Natl. Acad. Sci. USA, Vol. 74, 5463 (1977)], and the nucleotide sequences thereof were determined based on the data of an electrophoresis with an 8% urea-modified polyacrylamide gel and autoradiography.

As a result, it has been found that the DNA sequence of the gene encoding an esterase originated from *Serratia marcescens* Sr41 is composed of 1839 base pairs from the initiation codon ATG to the codon GCC.

Besides, the amino acid sequence determined from the nucleotide sequence is shown in SEQ ID NO: 3. The N-terminal Met in this amino acid sequence was not found at the N-terminus of amino acid sequence of the purified enzyme product of the Serratia-origin esterase, which will be caused by removal of N-terminal methionine from the protein produced in the cells by methionine aminopeptidase present in the cells. Moreover, although Serratia-origin esterase is an extra-cellular enzyme, it has no signal peptide which is usually present at the N-terminus of secretory proteins.

Example 4

*Serratia marcescens* Sr41 (FERMBP-487) was incubated in a nutrient medium (glucose 0.5%, peptone 1.0%, meat extract 0.3%, yeast extract 1.0%, and sodium chloride 0.5%, pH 7.0, 3 ml) overnight, and the culture thus obtained (0.1 ml) was inoculated in a fresh medium (3 ml) of the same nutrient medium as above, which was incubated at 30° C. for 3 hours, and after adding thereto NTG in a concentration of 0.1 mg/ml, was further incubated for additional 30 minutes. The culture broth was centrifuged, and the cells thus obtained were washed three times with a physiological saline solution (by centrifugation method). The cells thus obtained were suspended in a physiological saline solution and spread onto an LBG plate medium containing tributyrin 0.5%, glucose 2% and EDTA 2 mM in an amount of 1–1000 cells/one plate. After incubating at 30° C. for one day, the colony forming a large clear zone was collected to give *Serratia marcescens* M-1 strain (FERM P-12833). The thus-obtained mutant strain (one platinum loop) was inoculated to an esterase-producing medium containing ampicillin (500 μg/ml) and subjected to reciprocating shaking culture (shaking amplitude 7 cm, 120 r.p.m.) at 30° C. for 20 hours. The culture broth was centrifuged to give a supernatant having an esterase activity of about $80 \times 10^3$ unit/ml (measured by the convenient method). This strain had about 2.5 times higher esterase productivity than the parent host strain *Serratia marcescens* Sr41.

In the same manner as described in Examples 1 to 3, the chromosomal DNA was isolated from the above *Serratia marcescens* M-1, and the sequence was analyzed. As a result, it had a nucleotide sequence as shown in SEQ ID NO: 2. As is clear therefrom, the sequence was the same as the DNA sequence of that obtained from *Serratia marcescens*

Sr41 except that the 9th base was different, that is, it was composed of 1839 base pairs from the initiation codon ATG to the codon GCC. The amino acid sequence determined therefrom was the same as that deduced from SEQ ID NO: 1.

Example 5

Preparation of a strain having high esterase productivity:

The plasmid pLIPE111 was introduced into a restriction endonuclease-deficient strain, *Serratia marcescens* TT392, to give a transformed strain. The pLIPE111 plasmid DNA modified with *Serratia marcescens* was extracted from the cells of the transformed strain by alkaline lysis method. Then, *Serratia marcescens* Sr41 cells were transformed with the plasmid DNA obtained above by electroporation method to give a transformant *Serratia marcescens* TA5025 (FERM P-12607). The thus-obtained transformant (one platinum loop) was inoculated to an esterase-producing medium containing ampicillin (500 µg/ml) and subjected to reciprocating shaking culture (shaking amplitude 7 cm, 120 r.p.m.) at 30° C. for 20 hours. The culture broth was centrifuged to give a supernatant having an esterase activity of about $1.9 \times 10^2$ unit/ml (measured by the convenient method). This strain had about 6 times higher esterase productivity than the host strain *Serratia marcescens* Sr41.

Example 6

Production of esterase:

An esterase-producing medium (20 liters) containing ampicillin (500 µg/ml) was charged into a 30 liter-volume jar fermenter and was sterilized. Previously, the above *Serratia marcescens* TA5025 was incubated in the same medium by reciprocating shaking culture at 30° C. for 20 hours in the same manner as above. The pre-culture broth thus obtained (200 ml) was inoculated to the above medium and incubated under aeration at 30° C. with stirring at 200 r.p.m., 0.5 vvm for 18 hours. The culture broth was centrifuged to remove the cells, and the supernatant (18 liters) was concentrated with a ultrafilter (AIL-1010, manufactured by Asahi Chemical Industry Co., Ltd.) to give a crude enzyme solution (2000 ml) which had an esterase activity of $1.7 \times 10^6$ unit/ml (measured by the convenient method).

Example 7

Production of esterase:

An esterase-producing medium (20 liters) was charged into a 30 liter-volume jar fermenter and was sterilized. Previously, *Serratia marcescens* M-1 was incubated in the same medium by reciprocating shaking culture at 30° C. for 20 hours in the same manner as above. The pre-culture broth thus obtained (200 ml) was inoculated to the above medium and incubated under aeration at 30° C. with stirring at 200 r.p.m., 0.5 vvm for 18 hours. The culture broth was centrifuged to remove the cells, and the supernatant (18 liters) was concentrated with a ultrafilter (AIL-1010, manufactured by Asahi Chemical Industry Co., Ltd.) to give a crude enzyme solution (2000 ml) which had an esterase activity of $7.9 \times 10^5$ unit/ml (measured by the convenient method).

Effects of the Invention

The mutant strain and the transformant containing a recombinant plasmid inserted with a gene encoding an esterase of the present invention have excellent esterase productivity, and the cultivation of the transformant can give the desired esterase in high purity on a large scale.

---

What is claimed is:

1. A transformant *Serratia marcescens* which contains a recombinant plasmid comprising a plasmid containing a gene encoding an esterase, wherein said gene has the DNA sequence as shown in SEQ. ID NO: 1 or in SEQ. ID NO: 2.

2. A transformant *Serratia marcescens* TA5025 (FERM BP-4067).

3. A mutant strain *Serratia marcescens* M-1 (FERM BP-4068).

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1839 base pairs
        ( B ) TYPE: nucleic acid
        ( C ) STRANDEDNESS: double
        ( D ) TOPOLOGY: linear     ( i i ) MOLECULE TYPE: genomic DNA     ( i i i ) HYPOTHETICAL:

( i v ) ANTI-SENSE:

( v i ) ORIGINAL SOURCE:
        ( A ) ORGANISM:
        ( B ) STRAIN: Serratia marcescens Sr41

( x i ) SEQUENCE DESCRIPTION: SEQ ID NO:1:

```
ATG  GGC  ATC  TTT  AGC  TAT  AAG  GAT  CTG  GAC  GAA  AAC  GCG  TCA  AAG  GCG      48

CTG  TTT  TCC  GAC  GCC  TTG  GCC  ATC  TCT  ACC  TAC  GCT  TAC  CAC  AAT  ATC      96

GAT  AAC  GGC  TTC  GAT  GAA  GGC  TAT  CAC  CAG  ACC  GGT  TTC  GGC  CTC  GGT     144

CTG  CCG  CTG  ACG  CTG  ATC  ACG  GCG  CTC  ATC  GGC  AGC  ACC  CAG  TCG  CAG     192

GGC  GGC  CTG  CCC  GGT  CTT  CCC  TGG  AAC  CCC  GAC  TCC  GAA  CAG  GCC  GCG     240
```

```
CAG GAC GCG GTG AAC AAT GCC GGC TGG TCA GTG ATC GAC GCC GCG CAA    288
TTG GGA TAC GCC GGC AAA ACC GAT GCG CGC GGC ACC TAC TAC GGC GAA    336
ACC GCC GGT TAC ACC ACC GCT CAG GCC GAG GTG CTG GGC AAA TAT GAC    384
AGC GAA GGC AAT CTC ACC GCC ATT GGC ATC TCA TTT CGC GGT ACC AGC    432
GGC CCG CGC GAG TCG CTG ATC GGC GAT ACC ATC GGC GAT GTG ATT AAC    480
GAT CTG TTG GCC GGG TTC GGG CCG AAA GCT ATG CGA CGC TAT ACG CTG    528
AAG GCC TTC GGC AAT TTG CTG GGG GAC GTG GCG AAA TTC GCG CAG GCC    576
CAC GGG CTG AGC GGC GAA GAC GTG GTG ATC AGC GGC CAC AGC CTC GGC    624
GGG CTG GCG GTC AAC AGC ATG GCG GCG CAG AGC GAC GCA ACC TGG GGC    672
GGC TTC TAC GCG CAG TCC AAC TAT GTC GCC TTC GCC TCG CCG ACC CAG    720
TAC GAA GCC GGC GGC AAG GTG ATC AAC ATC GGC TAT GAG AAC GAT CCG    768
GTG TTT CGC GCG CTC GAC GGC ACC TCG CTG ACC CTG CCG TCA TTG GGC    816
GTT CAC GAT GCG CCG CAT ACC TCC GCC ACC AAC AAT ATC GTC AAC TTC    864
AAC GAC CAC TAC GCG TCG GAC GCC TGG AAT CTG TTG CCG TTC TCC ATT    912
CTC AAC ATT CCG ACC TGG CTA TCC CAC CTG CCG TTC TTC TAT CAG GAT    960
GGT CTG ATG CGG GTG CTG AAC TCC GAG TTT TAT TCG CTG ACC GAC AAA   1008
GAC TCG ACC ATC ATC GTC TCC AAC CTG TCG AAC GTC ACG CGC GGC AGT   1056
ACC TGG GTG GAA GAT CTG AAC CGC AAC GCG GAA ACG CAC AGC GGG CCG   1104
ACG TTT ATC ATC GGC AGC GAC GGC AAT GAT TTG ATC AAG GGC GGC AAA   1152
GGC AAC GAC TAT CTC GAG GGC CGC GAC GGT GAC GAT ATC TTC CGC GAC   1200
GCC GGC GGC TAT AAC CTG ATC GCC GGC GGC AAA GGC CAC AAT ATC TTC   1248
GAT ACC CAG CAG GCG TTG AAA AAC ACC GAG GTC GCC TAC GAC GGC AAT   1296
ACG CTT TAC CTG CGC GAC GCC AAA GGC GGC ATT ACG CTG GCG GAC GAC   1344
ATC AGC ACC CTG CGC AGC AAA GAA ACC TCC TGG CTG ATT TTC AGC AAA   1392
GAG GTG GAT CAT CAG GTG ACC GCC GCC GGA TTG AAA TCG GAT TCG GGC   1440
CTC AAA GCC TAT GCG GCC GCC ACC ACC GGC GGC GAC GGC GAT GAC GTC   1488
CTG CAG GCT CGC AGC CAC GAC GCC TGG CTG TTC GGC AAC GCC GGC AAC   1536
GAC ACG CTT ATC GGC CAT GCC GGC GGC AAC CTG ACC TTC GTC GGC GGC   1584
AGC GGC GAT GAC ATC CTG AAG GGG GTC GGC AAC GGC AAT ACC TTC CTG   1632
TTC AGC GGC GAT TTC GGC CGC GAC CAG CTG TAT GGC TTC AAC GCC ACC   1680
GAC AAA CTG GTA TTT ATC GGC ACC GAG GGC GCC AGC GGG AAT ATC CGC   1728
GAC TAT GCC ACG CAG CAA AAC GAC GAT CTG GTG CTG GCC TTC GGC CAC   1776
AGC CAG GTC ACG CTG ATC GGC GTC TCG CTC GAT CAT TTC AAC CCC GAT   1824
CAG GTG GTG TTG GCC                                               1839
```

( 2 ) INFORMATION FOR SEQ ID NO:2:

( i ) SEQUENCE CHARACTERISTICS:
        ( A ) LENGTH: 1839 base pairs
        ( B ) TYPE: nucleic acid
        ( C ) STRANDEDNESS: double
        ( D ) TOPOLOGY: linear     ( i i ) MOLECULE TYPE: Genomic DNA     ( i i i ) HYPOTHETICAL:

( i v ) ANTI-SENSE:

( v i ) ORIGINAL SOURCE:
   ( A ) ORGANISM:
   ( B ) STRAIN: Serratia marcescens M-1

( x i ) SEQUENCE DESCRIPTION: SEQ ID NO:2:

```
ATG GGC ATT TTT AGC TAT AAG GAT CTG GAC GAA AAC GCG TCA AAG GCG        48
CTG TTT TCC GAC GCC TTG GCC ATC TCT ACC TAC GCT TAC CAC AAT ATC        96
GAT AAC GGC TTC GAT GAA GGC TAT CAC CAG ACC GGT TTC GGC CTC GGT       144
CTG CCG CTG ACG CTG ATC ACG GCG CTC ATC GGC AGC ACC CAG TCG CAG       192
GGC GGC CTG CCC GGT CTT CCC TGG AAC CCC GAC TCC GAA CAG GCC GCG       240
CAG GAC GCG GTG AAC AAT GCC GGC TGG TCA GTG ATC GAC GCC GCG CAA       288
TTG GGA TAC GCC GGC AAA ACC GAT GCG CGC GGC ACC TAC TAC GGC GAA       336
ACC GCC GGT TAC ACC ACC GCT CAG GCC GAG GTG CTG GGC AAA TAT GAC       384
AGC GAA GGC AAT CTC ACC GCC ATT GGC ATC TCA TTT CGC GGT ACC AGC       432
GGC CCG CGC GAG TCG CTG ATC GGC GAT ACC ATC GGC GAT GTG ATT AAC       480
GAT CTG TTG GCC GGG TTC GGG CCG AAA GCT ATG CGA CGC TAT ACG CTG       528
AAG GCC TTC GGC AAT TTG CTG GGG GAC GTG GCG AAA TTC GCG CAG GCC       576
CAC GGG CTG AGC GGC GAA GAC GTG GTG ATC AGC GGC CAC AGC CTC GGC       624
GGG CTG GCG GTC AAC AGC ATG GCG GCG CAG AGC GAC GCA ACC TGG GGC       672
GGC TTC TAC GCG CAG TCC AAC TAT GTC GCC TTC GCC TCG CCG ACC CAG       720
TAC GAA GCC GGC GGC AAG GTG ATC AAC ATC GGC TAT GAG AAC GAT CCG       768
GTG TTT CGC GCG CTC GAC GGC ACC TCG CTG ACC CTG CCG TCA TTG GGC       816
GTT CAC GAT GCG CCG CAT ACC TCC GCC ACC AAC AAT ATC GTC AAC TTC       864
AAC GAC CAC TAC GCG TCG GAC GCC TGG AAT CTG TTG CCG TTC TCC ATT       912
CTC AAC ATT CCG ACC TGG CTA TCC CAC CTG CCG TTC TTC TAT CAG GAT       960
GGT CTG ATG CGG GTG CTG AAC TCC GAG TTT TAT TCG CTG ACC GAC AAA      1008
GAC TCG ACC ATC ATC GTC TCC AAC CTG TCG AAC GTC ACG CGC GGC AGT      1056
ACC TGG GTG GAA GAT CTG AAC CGC AAC GCG GAA ACG CAC AGC GGG CCG      1104
ACG TTT ATC ATC GGC AGC GAC GGC AAT GAT TTG ATC AAG GGC GGC AAA      1152
GGC AAC GAC TAT CTC GAG GGC CGC GAC GGT GAC GAT ATC TTC CGC GAC      1200
GCC GGC GGC TAT AAC CTG ATC GCC GGC GGC AAA GGC CAC AAT ATC TTC      1248
GAT ACC CAG CAG GCG TTG AAA AAC ACC GAG GTC GCC TAC GAC GGC AAT      1296
ACG CTT TAC CTG CGC GAC GCC AAA GGC GGC ATT ACG CTG GCG GAC GAC      1344
ATC AGC ACC CTG CGC AGC AAA GAA ACC TCC TGG CTG ATT TTC AGC AAA      1392
GAG GTG GAT CAT CAG GTG ACC GCC GCC GGA TTG AAA TCG GAT TCG GGC      1440
CTC AAA GCC TAT GCG GCC GCC ACC ACC GGC GGC GAC GGC GAT GAC GTC      1488
CTG CAG GCT CGC AGC CAC GAC GCC TGG CTG TTC GGC AAC GCC GGC AAC      1536
GAC ACG CTT ATC GGC CAT GCC GGC GGC AAC CTG ACC TTC GTC GGC GGC      1584
AGC GGC GAT GAC ATC CTG AAG GGG GTC GGC AAC GGC AAT ACC TTC CTG      1632
TTC AGC GGC GAT TTC GGC CGC GAC CAG CTG TAT GGC TTC AAC GCC ACC      1680
GAC AAA CTG GTA TTT ATC GGC ACC GAG GGC GCC AGC GGG AAT ATC CGC      1728
```

```
GAC TAT GCC ACG CAG CAA AAC GAC GAT CTG GTG CTG GCC TTC GGC CAC    1776

AGC CAG GTC ACG CTG ATC GGC GTC TCG CTC GAT CAT TTC AAC CCC GAT    1824

CAG GTG GTG TTG GCC                                                 1839
```

( 2 ) INFORMATION FOR SEQ ID NO:3:

( i ) SEQUENCE CHARACTERISTICS:
        ( A ) LENGTH: 613 amino acids
        ( B ) TYPE: amino acid
        ( D ) TOPOLOGY:linear     ( i i ) MOLECULE TYPE: peptide     ( x i ) SEQUENCE DESCRIPTION: SEQ ID NO:3:

```
Met Gly Ile Phe Ser Tyr Lys Asp Leu Asp Glu Asn Ala Ser Lys Ala
 1               5                  10                  15

Leu Phe Ser Asp Ala Leu Ala Ile Ser Thr Tyr Ala Tyr His Asn Ile
            20                  25                  30

Asp Asn Gly Phe Asp Glu Gly Tyr His Gln Thr Gly Phe Gly Leu Gly
        35                  40                  45

Leu Pro Leu Thr Leu Ile Thr Ala Leu Ile Gly Ser Thr Gln Ser Gln
    50                  55                  60

Gly Gly Leu Pro Gly Leu Pro Trp Asn Pro Asp Ser Glu Gln Ala Ala
 65                  70                  75                  80

Gln Asp Ala Val Asn Asn Ala Gly Trp Ser Val Ile Asp Ala Ala Gln
                85                  90                  95

Leu Gly Tyr Ala Gly Lys Thr Asp Ala Arg Gly Thr Tyr Tyr Gly Glu
            100                 105                 110

Thr Ala Gly Tyr Thr Thr Ala Gln Ala Glu Val Leu Gly Lys Tyr Asp
        115                 120                 125

Ser Glu Gly Asn Leu Thr Ala Ile Gly Ile Ser Phe Arg Gly Thr Ser
    130                 135                 140

Gly Pro Arg Glu Ser Leu Ile Gly Asp Thr Ile Gly Asp Val Ile Asn
145                 150                 155                 160

Asp Leu Leu Ala Gly Phe Gly Pro Lys Ala Met Arg Arg Tyr Thr Leu
                165                 170                 175

Lys Ala Phe Gly Asn Leu Leu Gly Asp Val Ala Lys Phe Ala Gln Ala
            180                 185                 190

His Gly Leu Ser Gly Glu Asp Val Val Ile Ser Gly His Ser Leu Gly
        195                 200                 205

Gly Leu Ala Val Asn Ser Met Ala Ala Gln Ser Asp Ala Thr Trp Gly
    210                 215                 220

Gly Phe Tyr Ala Gln Ser Asn Tyr Val Ala Phe Ala Ser Pro Thr Gln
225                 230                 235                 240

Tyr Glu Ala Gly Gly Lys Val Ile Asn Ile Gly Tyr Glu Asn Asp Pro
                245                 250                 255

Val Phe Arg Ala Leu Asp Gly Thr Ser Leu Thr Leu Pro Ser Leu Gly
            260                 265                 270

Val His Asp Ala Pro His Thr Ser Ala Thr Asn Asn Ile Val Asn Phe
        275                 280                 285

Asn Asp His Tyr Ala Ser Asp Ala Trp Asn Leu Leu Pro Phe Ser Ile
    290                 295                 300

Leu Asn Ile Pro Thr Trp Leu Ser His Leu Pro Phe Phe Tyr Gln Asp
305                 310                 315                 320

Gly Leu Met Arg Val Leu Asn Ser Glu Phe Tyr Ser Leu Thr Asp Lys
```

|  |  |  | 325 |  |  |  |  | 330 |  |  |  | 335 |  |  |
|---|---|---|---|---|---|---|---|---|---|---|---|---|---|---|
| Asp | Ser | Thr | Ile 340 | Ile | Val | Ser | Asn | Leu 345 | Ser | Asn | Val | Thr | Arg 350 | Gly | Ser |
| Thr | Trp | Val 355 | Glu | Asp | Leu | Asn | Arg 360 | Asn | Ala | Glu | Thr | His 365 | Ser | Gly | Pro |
| Thr | Phe 370 | Ile | Ile | Gly | Ser | Asp 375 | Gly | Asn | Asp | Leu | Ile 380 | Lys | Gly | Gly | Lys |
| Gly 385 | Asn | Asp | Tyr | Leu | Glu 390 | Gly | Arg | Asp | Gly | Asp 395 | Asp | Ile | Phe | Arg | Asp 400 |
| Ala | Gly | Gly | Tyr | Asn 405 | Leu | Ile | Ala | Gly | Gly 410 | Lys | Gly | His | Asn | Ile 415 | Phe |
| Asp | Thr | Gln | Gln 420 | Ala | Leu | Lys | Asn | Thr 425 | Glu | Val | Ala | Tyr | Asp 430 | Gly | Asn |
| Thr | Leu | Tyr 435 | Leu | Arg | Asp | Ala | Lys 440 | Gly | Gly | Ile | Thr | Leu 445 | Ala | Asp | Asp |
| Ile | Ser 450 | Thr | Leu | Arg | Ser | Lys 455 | Glu | Thr | Ser | Trp | Leu 460 | Ile | Phe | Ser | Lys |
| Glu 465 | Val | Asp | His | Gln | Val 470 | Thr | Ala | Ala | Gly | Leu 475 | Lys | Ser | Asp | Ser | Gly 480 |
| Leu | Lys | Ala | Tyr | Ala 485 | Ala | Ala | Thr | Thr | Gly 490 | Gly | Asp | Gly | Asp | Asp 495 | Val |
| Leu | Gln | Ala | Arg 500 | Ser | His | Asp | Ala | Trp 505 | Leu | Phe | Gly | Asn | Ala 510 | Gly | Asn |
| Asp | Thr | Leu 515 | Ile | Gly | His | Ala | Gly 520 | Gly | Asn | Leu | Thr | Phe 525 | Val | Gly | Gly |
| Ser | Gly 530 | Asp | Asp | Ile | Leu | Lys 535 | Gly | Val | Gly | Asn | Gly 540 | Asn | Thr | Phe | Leu |
| Phe 545 | Ser | Gly | Asp | Phe | Gly 550 | Arg | Asp | Gln | Leu | Tyr 555 | Gly | Phe | Asn | Ala | Thr 560 |
| Asp | Lys | Leu | Val | Phe 565 | Ile | Gly | Thr | Glu | Gly 570 | Ala | Ser | Gly | Asn | Ile 575 | Arg |
| Asp | Tyr | Ala | Thr 580 | Gln | Gln | Asn | Asp | Asp 585 | Leu | Val | Leu | Ala | Phe 590 | Gly | His |
| Ser | Gln | Val 595 | Thr | Leu | Ile | Gly | Val 600 | Ser | Leu | Asp | His | Phe 605 | Asn | Pro | Asp |
| Gln | Val 610 | Val | Leu | Ala |  |  |  |  |  |  |  |  |  |  |  |